(12) United States Patent
Koniuk

(10) Patent No.: US 6,443,993 B1
(45) Date of Patent: Sep. 3, 2002

(54) SELF-ADJUSTING PROSTHETIC ANKLE APPARATUS

(76) Inventor: Wayne Koniuk, 2614 Montecresta Dr., Belmont, CA (US) 94002

( * ) Notice: Subject to any disclaimer, the term of this patent is extended or adjusted under 35 U.S.C. 154(b) by 34 days.

(21) Appl. No.: 09/816,902

(22) Filed: Mar. 23, 2001

(51) Int. Cl.[7] ............................. A61F 2/48; A61F 2/66
(52) U.S. Cl. ........................................ 623/24; 623/50
(58) Field of Search ........................... 623/24, 50, 53, 623/55, 56, 40

(56) References Cited

U.S. PATENT DOCUMENTS

| | | | |
|---|---|---|---|
| 3,871,032 A | 3/1975 | Karas | 3/1.2 |
| 3,995,324 A | 12/1976 | Burch | 3/1.2 |
| 4,053,952 A | 10/1977 | Goldstein | 3/1.1 |
| 4,876,944 A | * 10/1989 | Wilson et al. | 91/35 |
| 5,112,296 A | * 5/1992 | Beard et al. | 602/28 |
| 5,269,811 A | 12/1993 | Hayes et al. | 623/3 |
| 5,421,426 A | * 6/1995 | De Beaucourt et al. | 180/8.1 |
| 5,667,715 A | 9/1997 | Foister | 252/62.52 |
| 5,711,746 A | 1/1998 | Carlson | 482/112 |
| 5,714,084 A | 2/1998 | Fujita et al. | 252/73 |
| 5,888,212 A | * 3/1999 | Petrofsky et al. | 623/24 |
| 5,957,981 A | 9/1999 | Gramnas | 623/47 |

\* cited by examiner

*Primary Examiner*—Bruce Snow
(74) *Attorney, Agent, or Firm*—Goldstein & Lavas, P.C.

(57) ABSTRACT

An auto-adjusting prosthetic ankle apparatus includes a base portion that is pivotally fixed to an attachment portion. The base portion is structured for being fixed to a foot blade, while the attachment portion is structured for fixing the prosthetic ankle apparatus to a lower leg portion of a prosthetic limb. The prosthetic ankle includes a computer controllable damping mechanism that is functionally and mechanically coupled between the base portion and the attachment portion. The damping mechanism enables a damping level to be selectively applied to lightly damp or heavily damp a relative motion between the base portion and the attachment portion as a user is walking to provide an auto-adjusting of the prosthetic ankle to changes in a ground surface being traversed and during various stages of a walking cycle.

15 Claims, 5 Drawing Sheets

SELF-ADJUSTING PROSTHETIC ANKLE APPARATUS

TECHNICAL FIELD

The present invention relates most generally prosthetic limbs. More particularly, the invention provides an improved ankle prosthesis that automatically adjusts to and accommodates a variety of heel heights and surface slopes, most preferably with little or no input from a wearer.

BACKGROUND ART

It is well known that users of prosthetic legs must constantly deal with several important issues in order to achieve natural and comfortable walking. A first issue occurs when the user encounters a slope of a ground surface being traversed and walked over. A second issue is produced by changes in the effective 'heel height' of differing shoes worn over prosthetic feet of a prosthetic limb. Until recently, a common approach was to physically change the foot on the prosthesis, or exchange the entire prosthetic leg when the need for differing heel heights arises. Changes in a ground slope had simply to be tolerated as an uncomfortable reality of prosthetic leg use. For completeness, a. discussion of these issues and specific details associated with changes in heel height, and equivalently, a change in a slope being traversed by an amputee, will now be briefly presented.

The inability to change heel heights causes many physical and safety problems. As an example, consider a 'below-the-knee' amputee. As shown in FIG. 1A, if the heel height of a prosthetic foot/limb is increased at A, an upper portion of the prosthetic leg is forced forward, for example at B. This results in a forwardly directed force or pressure being exerted upon the knee of the wearer. Accordingly, the knee would then have to be stabilized by repeated and possibly excessive use of the quadriceps muscle. Such activities and forces will certainly result in skin irritation, and possibly in blisters and or ulceration of tissue in contact areas.

Similarly, if a heel is lowered, as can be seen in FIG. 1B, a rearwardly oriented force is exerted upon the knee, tilting the leg backwards. In this scenario, there is a possibility of that the wearer will hyper-extend the knee, have difficulty in walking over a now stiff toe lever, and may lead to ligament damage. It may be noted that when considering an above-the-knee amputee, an analogous set of scenarios exist and leads to similar discomforts and injuries.

Another aspect of heel height changes is associated with changes in a slope of a ground surface being walked over and traversed. As is known to prosthetists and other skilled individuals, artificial limbs are essentially designed to be used over smooth and horizontal surfaces. They may function adequately when a wearer has to traverse a short, slight incline. However, each time a hill, ramp, or inclined drive or walkway of any significance is encountered, the above noted problems come to into play. Indeed, step inclines are essentially not traversable without resorting to possibly dangerous and embarrassing maneuvers such as walking sideways with the longitudinal length of the foot perpendicular to the direction of motion.

At present, mechanical heel adjusting means and methods have been difficult to set or calibrate, and do not solve the problem regarding an automatic adjusting to heel height changes, or inclining and declining surfaces. Recently, several noteworthy attempts have been made to address the above described problems and associated issues. However, each of these inventions discloses devices that are quite complicated in structure, and while useful for their intended purposes, do not exhibit the features and advantages of the present invention. For example, these devices have been found to be noisy, heavy, and/or of low reliability. Yet other currently available prosthetic limbs require a wearer to press buttons each time a change occurs in a slope being traversed. This can be very inconvenient, especially in hilly and crowded locations, and may prove embarrassing to some users.

Therefore, skilled individuals will understand a need for simplified, improved, and efficient prosthetic ankle architectures. In particular, there is a need for improved automatically and continually adjusting prosthetic ankles that are simple to operate and reliable. A full understanding of the present invention, including an understanding of a number of capabilities, characteristics, and associated novel features, will result from a careful review of the description and figures of several embodiments provided herein. Attention is called to the fact, however, that the drawings and descriptions are illustrative only. Variations and alternate embodiments are contemplated as being part of the invention, limited only by the scope of the appended claims.

SUMMARY OF THE INVENTION

In accordance with the present invention, an auto-adjusting prosthetic ankle apparatus includes a novel damping and. control arrangement. In a preferred embodiment, a base portion is structured for accepting and being fixed to a suitable foot blade. An attachment portion is provided for fixing the prosthetic ankle apparatus of the invention to a lower leg portion of a prosthetic limb. The attachment portion is pivotally fixed to the base portion, thereby enabling a pivoting or pivoting motion between the base portion, and items such as a foot blade that may be fixed thereto, with respect to the attachment portion. For example, a pivoting motion may include a range of plus/minus 10 to 30 degrees, and may enable a pivoting to any selected position between a first position and a second position.

The invention further includes a dynamically controllable damping means. The damping means is structured for functional coupling, or linking, of the base portion and the attachment portion. Importantly, the damping means is arranged to selectively allow unencumbered relative motion of the attachment portion or effectively prevent relative motion thereof, by selecting an amount or level of damping applied to any. relative motion between the base portion and the attachment portion to be one of either a first damping level or a second damping level. In addition, the actual damping level will most preferably be changeable in a rapid and virtually noise free fashion and provide a ratio of a second damping level to a first damping level of at least 10.

An electronics module is provided along with a sensing module including a plurality of sensing devices. The sensing devices enable the apparatus of the invention to determine when: (a) a portion of a prosthetic limb fixed to the attachment portion is moved to a pre-selected substantially vertical orientation, and (b) when a prosthetic foot of a user, which is coupled to the base portion, is contacting a ground surface being traversed by the user. As such, the sensing module may be configured with a level indicating device that may be fixed to the attachment portion (to determine when the orientation thereof is at the pre-selected substantially vertical orientation) and a ground surface contacting sensor.

Embodiments of the sensing module are to be structured for determining over what temporal intervals in a walking cycle the damping level is to be set to a first damping level and at what temporal intervals the damping level is to be set to a second damping level. As an astute observer will appreciate, the advantage of selectively and dynamically alternating between a first and second damping level may result in a much more natural gait and walking motion, along with the ability to automatically adjust the prosthetic ankle of the invention to changes in heel height and the slope of a ground surface being traversed. A preferred dynamic controlling of the damping means will result in a first damping level being established for a first interval of a walking cycle of a user, with a second damping level being established for a second interval (of the same walking cycle).

A control and computing means is included for receiving information from the sensing means for determining how and when a selected level of damping applied between the base portion and the attachment portion is to be altered. The control and computing means may be interfaced to a suitably miniaturized user interface, which may include one or more input devices (e.g., switches and pushbuttons) and one or more output devices such as a small display or annunciator elements.

As will be discussed in great detail hereinafter, the most preferred embodiments of the dynamically controllable damping means will include a hydraulic system including one or more hydraulic cylinders providing a plurality of hydraulically coupled internal pressure cylinders. A preferred form of realizing the dynamically controlled damping of pivoting motion between the base portion and the attachments structure simply controls the flow of fluid that is transferred from a first internal pressure chamber to a second internal pressure chamber. In a most preferred embodiment of the hydraulic system of the invention, magnetorheological fluids are employed to selectively, quietly and rapidly vary the damping level between the first level and the second level without the activation of any moving parts.

BRIEF DESCRIPTION OF THE DRAWINGS

In the drawings, like elements are assigned like reference numerals. The drawings are not necessarily to scale, with the emphasis instead placed upon the principles of the present invention. Additionally, each of the embodiments depicted are but one of a number of possible arrangements utilizing the fundamental concepts of the present invention. The drawings are briefly described as follows.

PARTIAL LIST OF REFERENCE NUMERALS

10 —auto adjust ankle apparatus
14 —foot blade or base
16a—illustrative foot
16b—illustrative ankle joint
16c—illustrative lower leg portion
18—base portion
22—main ankle pivot
26—ankle pivot post
28—pylon
30—pylon clamp
32—coil or magnetic coil
34—attachment portion or attachment structure
40—ground surface
48—dynamic damping means
50a—first hydraulic cylinder
50b—second hydraulic cylinder
52—hydraulic cylinder casing
56—piston
58—internal pressure chamber
60—mounting support and bumper
64—(fluid) transfer conduit
64a—first end of 64
64b—second end of 64
67—plate
100—electronics module
102—control and computing module
104—microcontroller
105—electronic switch
106—user interface
110—inclinometer module
112—ground surface contact sensor
116—power module
116a—power regulator and changing circuit
120 —electronic coupling or link

DETAILED DESCRIPTION AND MODES OF THE INVENTION

It is important to establish a definition for several terms and expressions that will be used throughout this disclosure. The terms 'ankle' or 'ankle joint' as employed herein may be assumed to be an arrangement including a base portion structured for accepting and being fixed to a foot blade, an attachment portion structured for fixing to a lower portion of a prosthetic limb/leg, and a pin and or pivot arrangement enabling a pivoting motion between the base portion and the attachment portion. The terms 'dynamically controlled damping level' and 'damping level' are to be understood to indicate that, in real-time, a level of damping applied resisting motion between the base portion and the attachment portion can be changed, most preferably in a rapid, step-wise manner. As such, the damping is not fixed and will assume one of a plurality of available damping levels, each applied for differing portions of a walk cycle. The term 'walk cycle' may be assumed to indicate the time interval and associated motions that result from an individual talking one full step with one leg. The cycle can be defined to start at any point in the series of motions discretely illustrated by example in FIG. 2, and is assumed to be substantially cyclic and periodic in nature. This term will be further discussed and defined below via examples. Other important terms and definitions will be provided as they are needed, to properly and concisely define the present invention and its associated novel characteristics and features.

Figure 1B:
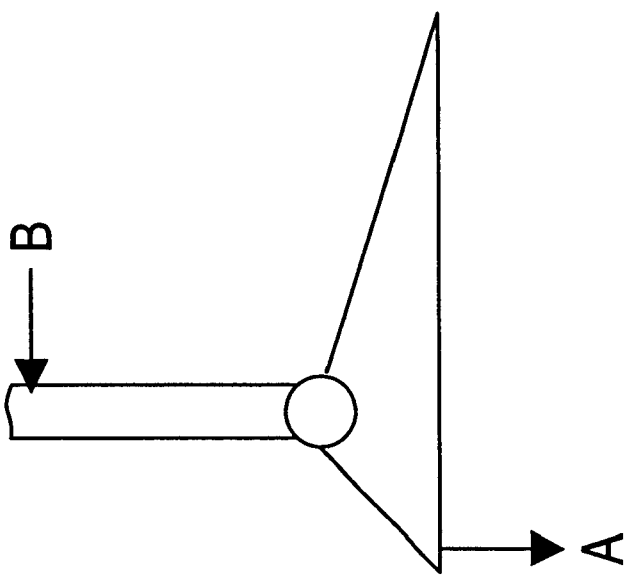
FIGS. 1A and 1B provide prior art illustrations for forces generated and exerted by changes in heel height of a wearer of a prosthetic limb.
Figure 1A:
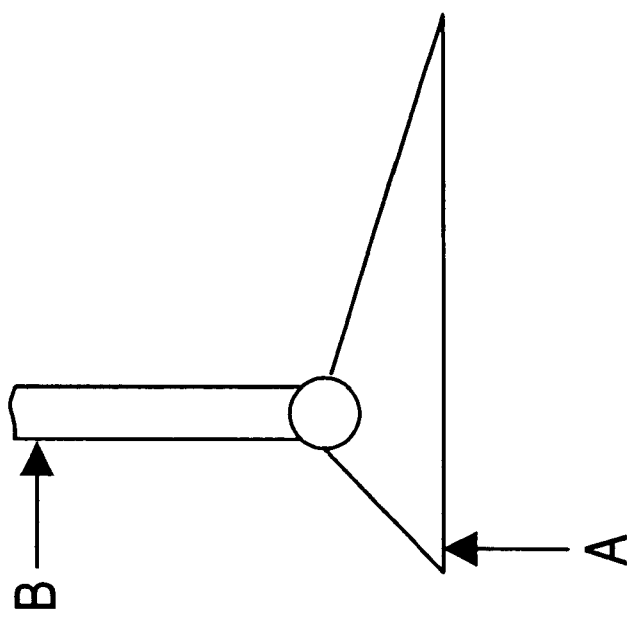
Figure 2A:
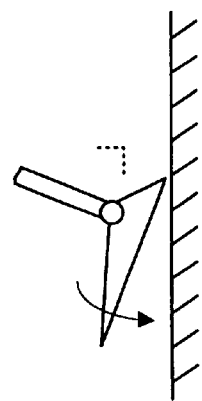
FIGS. 2A through 2F provide a series of depictions of important instants during a walking cycle of a prosthetic ankle and foot.
Figure 2B:
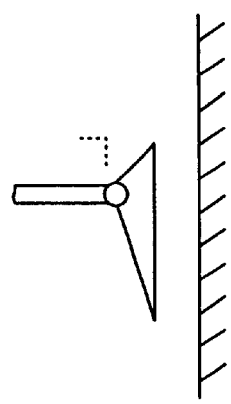
Figure 2C:
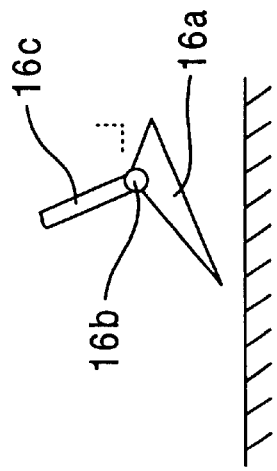
Figure 2D:
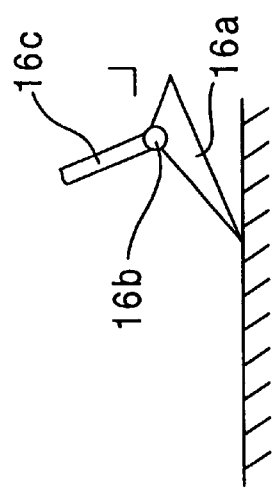
Figure 2E:
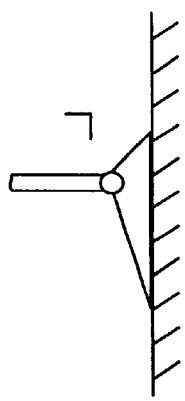

Referring now to the drawings, FIGS. 2A through 2F provide a plurality of depictions illustrating discreet movements and moments in a typical or preferred walk cycle. As can be seen in FIG. 2A, the depicted walk cycle may commence at the. end of the previous cycle, when a wearer or user of the auto-adjusting ankle apparatus 10 of the invention lifts an illustrated foot 16a from a ground surface 40. At this point the damping level may be dynamically altered and set to a first damping level, which is preferably a low damping level. This lower damping level allows the foot 16a to easily flex with respect to the lower leg portion 16c. This first damping level, as will be addressed shortly, will be maintained for a portion of the walking cycle that may be termed 'a first interval' or 'first temporal interval'. Alternately, the damping level may be set to a first damping level when an illustrative lower leg portion 16c is detected passing a pre-selected vertical orientation, such as a plumb vertical position, as depicted in FIG. 2B, or when the foot first contacts the ground, as depicted in FIG. 2D. Regardless, of when the first damping level is established, the lifted foot may then be moved forwardly, as depicted in FIGS. 2B and 2C, until the foot again contacts the ground surface 40. Importantly, the first damping level must be established when the user's foot contacts the ground, as shown in FIG. 2C. As can be seen in FIG. 2D, in the next instance, the illustrated foot 16a pivots around an ankle joint 16b, and quite soon thereafter flushly and fully contacts the ground surface 40. The foot must be allowed to pivot easily, until the illustrated lower leg portion 16c assumes a pre-selected vertical orientation (e.g., a plumb vertical position) as shown in FIG. 2E. At this point, the damping level should be set to the second, significantly greater, damping level to effectively prevent pivoting of the foot. The relative "stiffness" of the foot at this point is necessary to allow the foot to provide a stable "grounding" while the user takes a step with the other foot. It may be noted that the term 'significantly greater', as applied to the relationship between the two damping levels, will most preferably provide a ratio of the second damping level to the first damping level of approximately and substantially 10 or more. Further, it should be understood that preferably a damping controlling means and structures associated therewith will enable preferred damping levels to be maintained or consistently established regardless of commonly encountered, changeable parameters, such as ambient temperature, humidity, etc. In addition, it may be noted that the change from the first damping level to the second damping level in FIG. 2E, results in the automatic auto-leveling of a foot fixed to the lower portion of the ankle apparatus 10 of the invention. In particular, waiting for the lower leg portion 16c to be plumb, rather than simply orthogonal to the foot allows the wearer to adapt to an incline, wherein the foot must flex past the orthogonal position, to a position where the foot actually forms an acute angle with the lower leg portion 16c. However, the precise moment when the second damping level is established, to "stiffen the ankle" should be when the lower leg portion 16c is vertical (plumb), since at this point the wearer can stably rest his weight upon that foot—regardless of the incline.

Figure 2F:
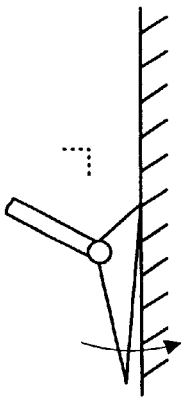

As skilled individuals will appreciate, once the second damping level is established in FIG. 2E, the wearer will continue the walking cycle—now with the illustrated ankle joint in a 'stiffened state', maintaining a possibly near orthogonal relationship between the illustrated foot 16a and the illustrated lower leg portion 16c (assuming the previous step was upon a level ground surface). This is depicted in FIGS. 2E and 2F. Finally, FIG. 2F transitions into FIG. 2A when the wearer lifts the illustrated foot 16a. Importantly, the structures of the invention enable the damping level applied to an ankle joint to be varied, and further determine when a plurality of damping levels should each be established to result in an more natural gait and walking motion.

Figure 3:
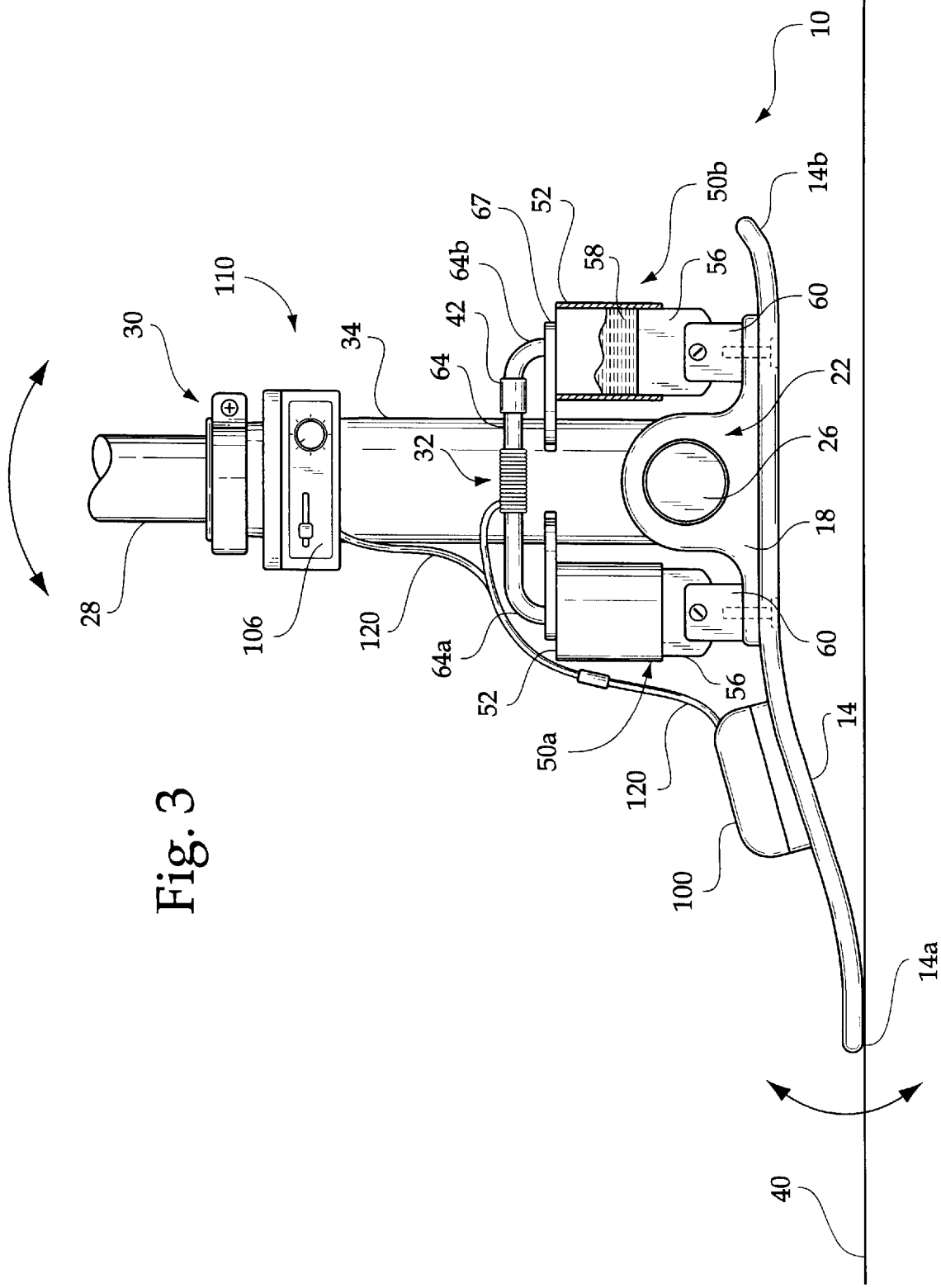
FIG. 3 is a diagrammatic, simplified elevational view of an embodiment of an auto-adjusting or auto-leveling prosthetic ankle in accordance with the present invention.

Turning now to FIG. 3 there is illustrated a diagrammatic, somewhat simplified profile view of an embodiment of an auto-adjusting or auto-leveling prosthetic ankle apparatus 10 in accordance with the present invention. For purposes of establishing consistency in conventions such as "clockwise" and "counterclockwise", the depicted ankle in FIG. 3. may be considered to be a right leg, as viewed from the inside, or a left leg, as viewed from the outside. As shown, the prosthetic ankle apparatus 10 may include a lower base portion 18 that is coupled via an ankle pivot pin 26 to an attachment portion 34. The portions of the apparatus forming the pivot location of the apparatus may be termed a 'main ankle pivot'. The base portion 18 is structured for accepting and having a foot blade 14 fixed thereto. The attachment portion 34 is structured for fixing the prosthetic ankle apparatus 10 to a lower leg portion of a prosthetic limb. For example, as illustrated in FIG. 3, an attachment portion 34, which is pivotally fixed to the base portion 18, may be arranged with a pylon clamp 30 to accept and securely couple to a common prosthetic pylon 28.

Figure 4:
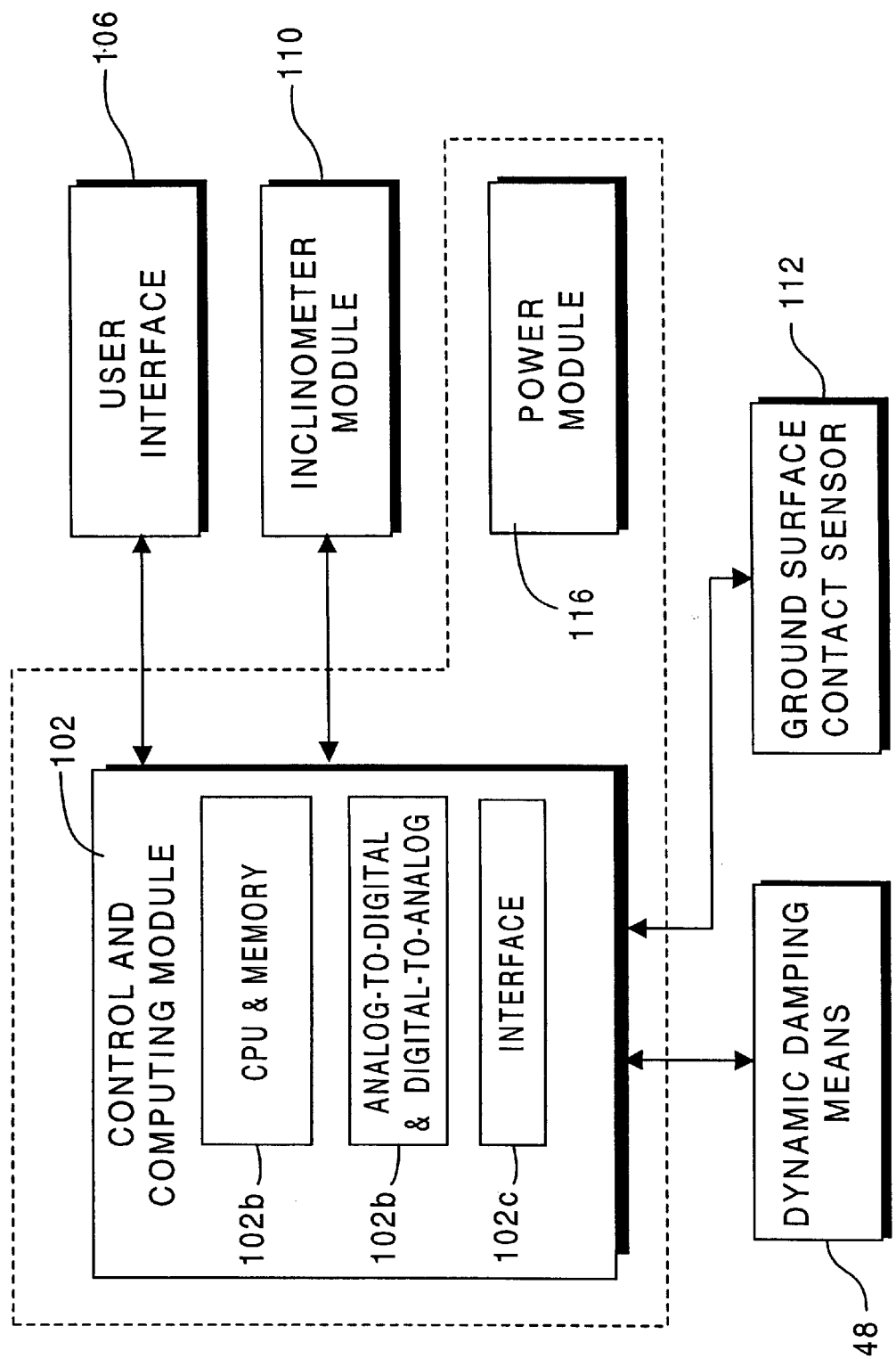
FIG. 4 is a high level block diagram of an embodiment of the invention that is consistent with the ankle depicted in FIG. 3.

The pivoting established by the ankle pivot post 26 enables a pivoting of the base portion 18, with respect to the attachment portion 34, to any position between a first position and a second position. Most preferably, an angularly measured pivot range will provide for a pivoting motion of plus and minus 10 to 30 degrees, respectively, from a plumb vertical position. A dynamically controllable damping means is included that is structured to enable a damping level to be established that affects the pivoting of the ankle apparatus 10, which is preferably directly and functionally coupled between the base portion 18 and the attachment portion 34. The dynamically controlled damping means 48, as shown in FIGS. 3 and 4, selectively enables a level of damping applied to a relative motion between the base portion 18 and the attachment portion 34 to be established at one of a first damping level or a second damping level, or possibly any level therebetween.

As illustrated in FIG. 3, preferred embodiments of the dynamically controllable damping means 48 will include a hydraulic system including one or more hydraulic cylinders providing a plurality of hydraulically coupled internal pressure cylinders. A most preferred form of damping is realized by a dynamically controlled damping of a pivoting motion of the ankle that simply controls a rate of flow of fluid that is transferred from a first internal pressure chamber 58 to a second internal pressure chamber. As such, when considering the structure of the embodiment depicted in FIG. 3, fluid is transferred from one hydraulic cylinder to a second by way of a fluidic coupling, which may be termed a fluid transfer conduit 64. As such, when the attachment portion 34 is pivoted in a counter clockwise direction, fluid is transferred from a first hydraulic cylinder 50a, which is positioned in front of the attachment portion 34 and closer to a front portion of an attachable foot blade 14. The fluid transferred from the first hydraulic cylinder 50a is coupled to a second hydraulic cylinder 50b that is positioned behind the attachment portion 34, closer to a heel portion of an attachable foot blade 14. Similarly, fluid is transferred in the opposite direction, from the second hydraulic cylinder 50b to the first hydraulic cylinder 50a as the attachment portion 34 is pivoted in a clockwise direction. It must be noted that such a structure enables a damping level to be established by simply altering the resistance to fluid flow through a fluid transfer conduit 64. Accordingly, any arrangement that is structured to control a flow rate at which fluid may be transferred from a first internal chamber to a second internal chamber, which thereby may be employed to select a first damping level or a second damping level to be available, is considered within the scope of the invention. Further, it is certainly possible to employ conventional damping control arrangements, including piezo-type values, controllable petcock arrangements, and other flow control mechanisms available and known to skilled persons who have studied this disclosure. However, a most preferred embodiment of the invention selectively enable a damping level to be changed from a first damping level to a second damping level employs magnetorheological (MR) fluids and the generation of magnetic fields, which is fully consistent with the structures of FIGS. 3 and 4. Specifically, this form of a damping means will enable a magnetic field that is generated in one of a number of fashions to change the viscosity of an MR fluid flowing through the transfer conduit 64; effectively varying the flow rate in a virtually silent fashion, using virtually no moving parts.

As such, a preferred dynamic damping selection means will include a magnetic field generating element responsive to the control and computing means for selectively establishing a magnetic field that penetrates the transfer conduit 64. A volume of magnetorheological (MR) fluid, with a portion of the volume located within a transfer conduit 64, or an equivalent passage way between internal pressure chambers 58, is influenced by the magnetic field generating element so that when a magnetic field having a first field strength is generated the first damping level is selected, and when a magnetic field having a second field strength is generated the second damping level is selected.

Accordingly, preferred embodiments of the invention will employ a control and computing module 102 for receiving and or exchanging information with a ground surface contact sensor 112 and an inclinometer module 110. The information may be processed to determine when a dynamic damping means 48 is employed to established the first damping level and the second damping level, using the principles described above, in addition to well known locomotive principles.

It may be noted that the user interface 106 may optionally be included, as required, to enable a user or wearer to make calibrating or operational adjustments to the circuits and modules of the auto-adjusting ankle apparatus 10 of the present invention, or to receive annunciations such as, for example, a low battery indication. As such, preferred embodiments of the user interface 106 may include one or more miniaturized input devices, such as switches and pushbuttons, and one or more very compact output devices such as a small display and or annunciator elements.

A preferred structure, as shown in FIG. 3, for generating a required magnetic field when magnetorheological (MR) fluids are employed, may be provided using a magnetic generating coil 32. The coil 32 is formed with by a coiling of a suitable gauge wire around a magnetically transparent fluid transfer conduit 64. An electronics module 100 is operatively coupled to the coil 32 to cause the energizing the coil 32 and generating of one or more suitable magnetic fields. The application of the magnetic field to MR fluid flowing through the transfer conduit 64, as understood by skilled persons familiar with MR fluids, results in the damping level selectively changing from a first, lower level, to a second higher damping level. In particular, though, by a most preferred embodiment, the second damping level is achieved by suitably energizing the coil 32 to stiffen the ankle once the pylon 28 is vertical, to allow the weight of the wearer to be supported upon the foot blade 14. In addition, the coil is substantially de-energized (or substantially less energized) to allow the foot to flex once it is lifted and then again contacts the ground surface.

Returning to FIG. 3, as can be seen therein, each of the first hydraulic cylinder 50a and the second hydraulic cylinder 50b includes a hydraulic cylinder casing 52. Each hydraulic cylinder casing 52 is structurally coupled to the attachment portion 34. For example, a mounting plate 67 may be employed, as well as many other providable arrangements and structures for such a coupling. As such, due to the inclusion of mounting plate 67 (or equivalents) the hydraulic cylinder casings are connected to, and will follow the motions of the attachment portion 34. Indeed, it is contemplated that the hydraulic cylinder casings 52 and the attachment portion 34 may be formed with a cast and possibly monolithic embodiment. As further shown, an internal pressure chamber 58 of the first hydraulic cylinder 50a is fluidly coupled to an internal pressure chamber 58 of the second hydraulic cylinder 50b via a fluid transfer conduit 64. Specifically, a first end 64a of the transfer conduit 64 is operatively coupled to receive and provide fluid to the internal chamber of the first hydraulic cylinder 50a, while a second end 64b of the transfer conduit 64 is operatively coupled to provide and receive fluid to an internal chamber of the second hydraulic cylinder 50b.

Returning again to FIG. 3, each hydraulic cylinder 50 is structured having a cylinder casing 52 and an associated piston 56. As shown, each hydraulic cylinder 50 forms and contains an internal pressure chamber 58 which results from a piston 56 being located within the casing, thereby establishing the internal chamber therein. One or more sealing rings (compression rings) may included for containing the hydraulic fluids within the hydraulic cylinders 50. A preferred mounting arrangement for fixing or coupling a lower portion of the piston 56 to the base portion 18 may include the use of a mounting and support bumper 60, which is most preferably somewhat flexible or yieldable.

Turning now to FIG. 4, there is illustrated therein a high level block diagram of a generalized embodiment of the invention that is consistent with the auto-adjusting ankle apparatus 10 depicted in FIG. 3. As shown, a sensing module is included for determining when: (1) a portion of a prosthetic limb fixed to the attachment portion 34 is in or passes a pre-selected vertical orientation, and (2) when a prosthetic foot of a user is contacting a ground surface 40. The sensing module is structured for providing information that may be employed to determine when the damping means is to be set to the first damping level, for a first temporal interval of a walking cycle of a user, and subsequently, when the second damping level should be established for a second interval of the walking cycle. In preferred embodiments, the sensor module would include an inclinometer, preferably provided as a solid-state accelerometer, and at least one ground surface contact sensor. A suitable ground surface contact sensing may be provided by a simple micro-switch or a load cell positioned to determine when the foot blade or a prosthetic foot fixed to and/or around the foot blade is contacting a ground surface 40.

Figure 5:
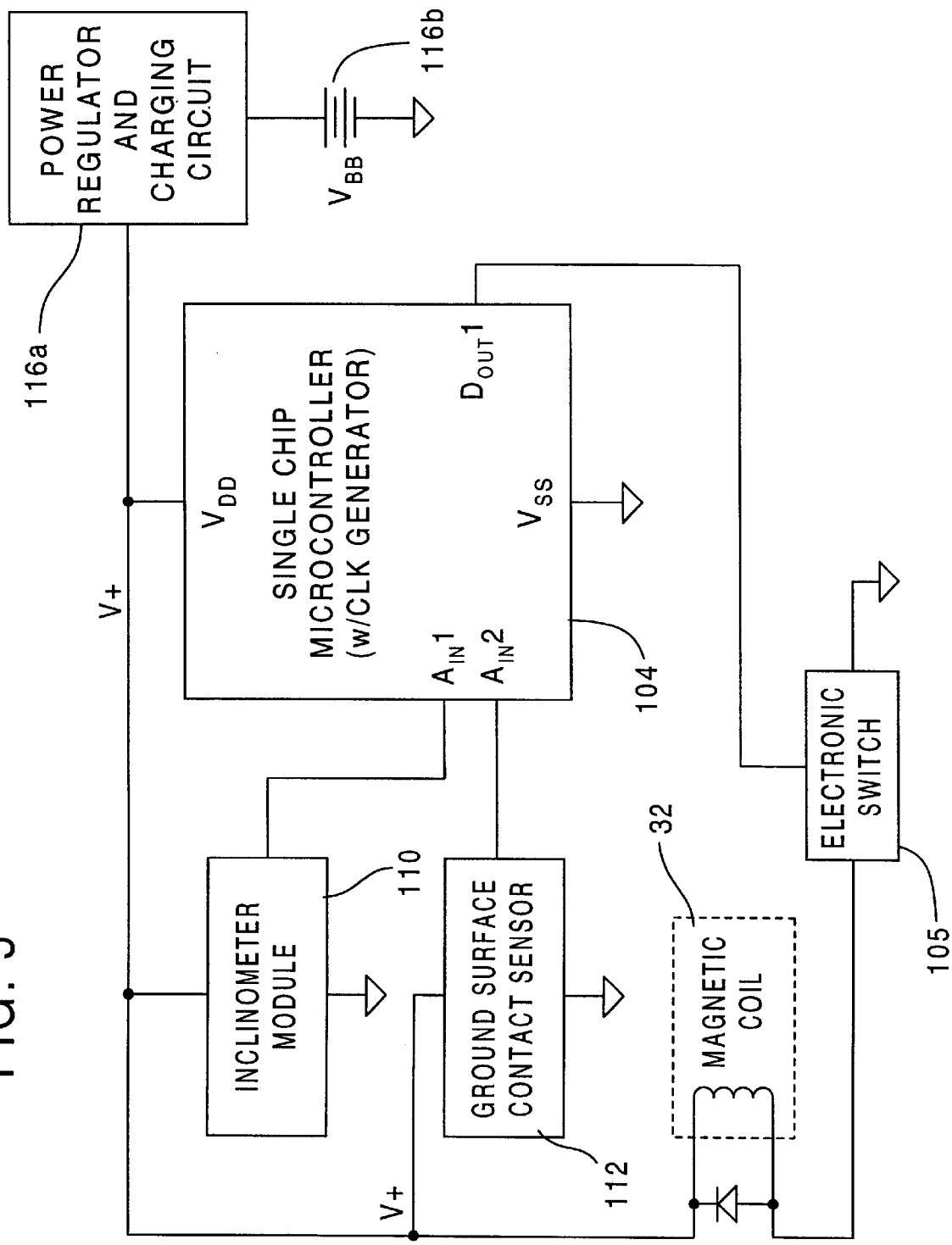
FIG. 5 provides a high level schematic diagram of a preferred embodiment auto-leveling ankle of the invention.

As can be further seen in FIG. 4, a control and computing module 102 is included, which may also be termed a 'control and computing means'. As shown, preferred embodiments of the control and computing module 102 may be structured with a CPU and memory 102b, required analog-to-digital and digital-to-analog circuitry 102b, and needed interface components 102c. In a most preferred embodiment of the invention, as shown in the schematic of FIG. 5, a single chip microcontroller 104 may be utilized at the control and computing module 102. Alternately, other complicated devices, such as field programmed gate arrays (FPGAs) and or application specific integrated circuits (ASICs) may be used to embody the control and computing module 102. Regardless of the specific construction actually employed, the control and computing module 102 of FIG. 4 is provided for receiving information from sensing means, including the ground surface contact sensor 112 and the inclinometer module 110, and determining from the received information when and for how long the. damping level applied between the base portion 18 and the attachment portion 34 is set to the first damping level and the second damping level.

It may be noted that the electronics module 100 of FIG. 3, which is contemplated to include items such as the control and computing module 102 and a power module 116, may be mounted upon a portion of the foot blade 14, or alternately mounted or included within a housing that is fixed to the attachment portion 34. When the electronics module 100 is mounted upon the attachment portion 34, it may most preferably contain items such as the inclinometer module 110, the user interface 106, batteries 116b, etc. This embodiment may then eliminate the need for the electronic couplings 120, that are illustrated in FIG. 3.

Returning to FIG. 4, a dynamic damping means 48 and a user interface 106 are shown. The damping means may be provided as discussed in FIG. 3, with a plurality of hydraulic cylinders having fluidic couplings therebetween. Alternately, a single hydraulic cylinder may be employed (not illustrated) having a plurality of internal pressure chambers 58, further having required fluidic couplings, through which the flow rate of fluid can be set to at least two levels, enabling the establishing of a first damping level and a second damping level.

A most preferred low cost embodiment of the invention employing a single chip microcontroller 104 is shown in FIG. 5. As can be seen in this high level schematic diagram, the microcontroller 104 includes many required components of the electronics module 100. For example, microcontroller 104 incorporates needed analog-to-digital and digital-to-analog circuitry and various interface components. As shown, this embodiment may be structured with analog inputs Ain1 and Ain2, as well as a digital on/off output Dout1. The analog inputs are used to operatively couple and sense information from the inclinometer module 110, the ground surface contact sensor 112, etc. The digital inputs may be arranged for controlling the magnetic coil 32 via a current boosting electronic switch 114, or less preferably a mechanical equivalent.

The auto-adjusting ankle apparatus 10 of the present invention is to be employed as a highly portable and compact apparatus that includes a fully self-contained power module 116. A most preferred embodiment of a power module 116 may be structured for use with rechargeable batteries, and is depicted in FIG. 5 as a power regulator and charging circuit 116a and a rechargeable battery 116b. Presently, the power regulator and charging circuit 116a may be provided by skilled persons in a very compact and lightweight construction employing a small number of electronic devices and or components. In addition, the rechargeable battery 116b is most preferably provided as a high capacity, high density power source. At present lithium-ion battery technology is preferred. In particular, the advent of solid electrolyte polymer-type lithium batteries provide a most desirable power source that is rugged and may be provided in a large variety of shapes. A possibly most preferred location for mounting one or more batteries 116b, may be within an interior space of the attachment portion 34.

While there have been described a plurality of the currently preferred embodiments of the present invention, those skilled in the art will recognize that other and further modifications may be made without departing from the invention and it is intended to claim all modifications and variations as fall within the scope of the invention and the appended claims.

What is claimed is:

1. An auto-adjusting prosthetic ankle apparatus, for attachment to a prosthetic limb having a lower portion, comprising:
   a) a base portion structured for fixing to a foot blade;
   b) an attachment portion structured for fixing to the lower portion of the prosthetic limb to the ankle apparatus, the attachment portion pivotally mounted to the base portion to enable a foot blade fixed to the base portion to be pivoted to any position, with respect to the attachment portion, between a first position and a second position;
   c) a dynamically controllable damping mechanism coupled between the base portion and the attachment portion, the damping mechanism including at least one hydraulic cylinder enabling a level of damping to be changed from a first damping level to a second damping level;
   d) a level indicating device for indicating when a longitudinal axis of the attachment portion of the prosthetic limb fixed thereto reaches a vertical orientation; and
   e) a control and computing module operatively coupled to the damping means to establish the level of damping selected from a group of damping levels consisting of:
      i) a first damping level, and
      ii) a second damping level.

2. The auto-adjusting prosthetic ankle in accordance with claim 1, wherein the control and computing module is configured to receive information from the level indicating device and thereby choose between the first damping level and second damping level.

3. The auto-adjusting ankle in accordance with claim 2, wherein the level indicating device is provided by a solid state inclinometer unit.

4. The auto-adjusting prosthetic ankle in accordance with claim 2, with the dynamically controllable damping mechanism comprising:
   a) a hydraulic system having a plurality of internal hydraulic pressure chambers, wherein a pivoting motion between the base portion and the attachment portion results in a transfer of fluid between a first internal hydraulic pressure chamber and a second internal hydraulic pressure chamber; and
   b) transfer means including a controllable fluid coupling established between the first internal hydraulic pressure chamber and the second internal hydraulic pressure chamber, wherein the controllable fluid coupling, under control of the control and computing module, selectively restricts the flow of a fluid between internal hydraulic pressure chambers, thereby selectively enabling a level of damping to be changed between a first damping level and a second damping level.

5. The auto-adjusting prosthetic ankle in accordance with claim 4, wherein each internal hydraulic pressure chamber is provided in a distinct hydraulic cylinder.

6. The auto-adjusting prosthetic ankle in accordance with claim 5, comprising two hydraulic cylinders.

7. An auto-adjusting prosthetic ankle apparatus, comprising:
   a) a base portion;
   b) an attachment portion for fixing the prosthetic ankle apparatus to a lower leg portion of a prosthetic limb, the attachment portion pivotally fixed to the base portion to enable pivoting of the attachment portion with respect to the base portion, to any position between a first position and a second position;

c) a dynamically controllable damping means structured for functionally coupling between the base portion and the attachment portion, the damping means selectively varying a degree of damping of the pivoting of the base portion with respect to the attachment portion to be one of either a first damping level or a second damping level;

d) a sensing module for detecting when:
   i) a pre-selected portion of a prosthetic limb fixed to the attachment portion is in a pre-selected vertical orientation; and
   ii) when a prosthetic foot of a user is contacting and not contacting a ground surface;

e) a control means structured for setting the damping means to the first damping level, for a first interval of a walking cycle of a user, and the second damping level for a second interval of the walking cycle as determined by detections of the sensing module.

8. The auto-adjusting ankle in accordance with claim 7, wherein the sensing means includes a level indicating device to determine when a prosthetic limb fixed to the attachment portion is in a pre-selected vertical orientation.

9. The auto-adjusting ankle in accordance with claim 8, wherein the second damping level creates greater resistance to pivoting of the base than the first damping level, wherein the pre-selected portion of the prosthetic limb is a vertical pylon, and wherein the second damping level is enabled when the vertical pylon is plumb.

10. The auto-adjusting ankle in accordance with claim 7, wherein the sensing means includes at least one of:
   a) a micro-switch for indicating to the control and computing means when ground contacting is occurring or not occurring, and
   b) a load cell installed in the either the attachment portion or a portion of a prosthetic limb fixed thereto; and
   wherein the first damping level is selected when the micro-switch indicates that the base has contacted the ground and while the pylon is not vertical.

11. The auto-adjusting ankle in accordance with claim 7, with the dynamically controllable damping means comprising:
   a) a hydraulic system having a plurality of hydraulic cylinders, including a first hydraulic cylinder and a second hydraulic cylinder, each hydraulic cylinder structured having a cylinder casing and an associated piston, with each hydraulic cylinder forming an internal pressure chamber;
   b) the first hydraulic cylinder positioned in front of the attachment portion, closer to a front portion of an attachable foot blade, while the second hydraulic cylinder is positioned behind the attachment portion, closer to a heel portion of an attachable foot blade;
   c) the casing of each respective hydraulic cylinder fixed to the attachment portion so as to pivot and move with the attachment portion, while each respective piston is coupled to the base portion, thereby forcing a first piston to increase a pressure within an associated internal chamber, while a second piston decreases pressure within a second internal chamber; and
   d) a transfer conduit arranged to provide a fluid coupling between the internal chamber of the first hydraulic cylinder and the internal chamber of the second hydraulic cylinder;
   e) the transfer conduit connecting the internal chambers of the first hydraulic cylinder and second hydraulic cylinder, including a dynamic damping structure, provided to selectively restrict the flow of a fluid flowing from one of the internal chambers in which pressure is increasing into the other of the internal chamber, the damping means operatively coupled to and responsive to the control means.

12. The auto-adjusting ankle in accordance with claim 11, wherein the damping means includes:
   a) a magnetic field generating element responsive to the control and computing means for selectively establishing a magnetic field that penetrates the transfer conduit and fluid passing therethrough; and
   b) a volume of magnetorheological fluid a portion of which is located within the transfer conduit and influenced by the magnetic field generating element so that when a magnetic field having a first field strength is generated the first damping level is established, and when a magnetic field having a second field strength is generated the second damping level is established.

13. The auto-adjusting ankle in accordance with claim 12, wherein the magnetic field generating element is provided by a magnetic coil that is formed with by coiling of a wire around a magnetically transparent fluid transfer conduit.

14. A damping and control apparatus for use with a prosthetic ankle, the damping and control apparatus connected between a base portion and an attachment portion of the prosthetic ankle, wherein the attachment portion is pivotally mounted to the base portion, with the damping and control apparatus enabling the dynamic damping of pivoting motion between the base portion and the attachment portion, the damping and control apparatus comprising:
   a) a dynamically controllable damping means functionally coupled between the base portion and the attachment portion, the damping means comprising at least one hydraulic cylinder providing a plurality of internal pressure chambers enabling a level of damping to be changed from a first damping level to a second damping level;
   b) a level indicating device for indicating when a longitudinal axis of the attachment portion of a prosthetic limb fixed thereto reaches a pre-selected vertical orientation;
   c) a control and computing module operatively coupled to the damping means to establish a level of damping selected from a group of damping levels consisting of:
      i) a first damping level, and
      ii) a second damping level; and
   d) a ground surface contacting device operatively coupled to the control and computing module to indicate when a prosthetic foot of the prosthetic ankle is contacting and not contacting a ground surface.

15. The damping and control apparatus as recited in claim 14, wherein the control and computing module selects the second damping level in response to the level indicating device indicating that the attachment portion is vertical and selects the first damping level when the level indicating device is not vertical.

* * * * *